(12) United States Patent
Wei et al.

(10) Patent No.: US 7,790,401 B2
(45) Date of Patent: Sep. 7, 2010

(54) METHODS FOR DETECTION OF IMMUNOSUPPRESSANT DRUGS

(75) Inventors: Tie Q. Wei, Bear, DE (US); Gerald Siefring, Jr., Wilmington, DE (US); Christy Schaible, Oxford, PA (US); Amy Posey, Cochranville, PA (US)

(73) Assignee: Siemens Healthcare Diagnostics, Deerfield, IL (US)

( * ) Notice: Subject to any disclaimer, the term of this patent is extended or adjusted under 35 U.S.C. 154(b) by 293 days.

(21) Appl. No.: 11/834,173

(22) Filed: Aug. 6, 2007

(65) Prior Publication Data

US 2009/0042223 A1 Feb. 12, 2009

(51) Int. Cl.
*G01N 33/53* (2006.01)

(52) U.S. Cl. ..................... 435/7.1; 436/518

(58) Field of Classification Search ............... None
See application file for complete search history.

(56) References Cited

U.S. PATENT DOCUMENTS

| | | | |
|---|---|---|---|
| 4,273,867 A | 6/1981 | Lin et al. | |
| 5,135,875 A | 8/1992 | Meucci et al. | |
| 5,650,288 A | 7/1997 | MacFarlane et al. | |
| 6,054,303 A * | 4/2000 | Davalian et al. | 435/188 |
| 6,153,442 A * | 11/2000 | Pirio et al. | 436/533 |
| 6,171,801 B1 | 1/2001 | Staples et al. | |
| 6,190,873 B1 | 2/2001 | Davalian et al. | |
| 6,790,668 B1 | 9/2004 | Ferreira et al. | |
| 6,887,669 B1 | 5/2005 | Staples et al. | |
| 7,186,518 B2 | 3/2007 | Wang et al. | |
| 2004/0185110 A1 * | 9/2004 | Harland et al. | 424/489 |
| 2005/0112778 A1 | 5/2005 | Wang et al. | |
| 2006/0147525 A1 * | 7/2006 | Sung | 424/464 |
| 2007/0065479 A1 * | 3/2007 | Zhang et al. | 424/423 |
| 2007/0087396 A1 | 4/2007 | Konrath et al. | |

OTHER PUBLICATIONS

Boer, et al., Clin Biochem. Oct. 2006; 39(10); 1041-1043.
Kuzuya, et al., Ther Drug Monit. Aug. 2002; 24(4): 507-511.
Armendariz, et al., Ther Drug Monit. Dec. 2005; 27(6): 766-769.

* cited by examiner

*Primary Examiner*—Jacob Cheu
(74) *Attorney, Agent, or Firm*—Theodore J. Leitereg

(57) ABSTRACT

Methods and reagents are disclosed for enhancing the bioavailability of a hydrophobic drug, and in some embodiments for determining a hydrophobic drug, in a sample suspected of containing a hydrophobic drug. A combination is formed in a medium where the combination comprises the sample, a hemolytic agent where a determination of the hydrophobic drug is conducted, and a bioavailability agent for the hydrophobic drug. The bioavailability agent comprises an ionic detergent comprising a chain of at least 10 carbon atoms or a non-ionic detergent comprising a chain of at least 15 repeating ethylene oxide units or propylene oxide units or a combination of ethylene oxide units and propylene oxide units. The concentration of the bioavailability agent in the medium is sufficient to enhance the bioavailability of the hydrophobic drug. The medium is incubated under conditions for enhancing the bioavailability of the hydrophobic drug, and in a determination of the hydrophobic drug under conditions for hemolyzing cells in the sample. For determination of the hydrophobic drug, reagents for determining the presence and/or amount of the hydrophobic drug in the sample are added to the medium. The reagents comprise at least one antibody for the hydrophobic drug. The medium is examined for the presence of a complex comprising the hydrophobic drug and the antibody for the hydrophobic drug. The presence and/or amount of the complex indicates the presence and/or amount of the hydrophobic drug in the sample.

11 Claims, No Drawings

METHODS FOR DETECTION OF IMMUNOSUPPRESSANT DRUGS

BACKGROUND

The invention relates to compounds, methods and kits for the determination of hydrophobic drugs such as, for example, immunosuppressant drugs, in samples, such as patient samples, known or suspected to contain one or more of such hydrophobic drugs.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because the distribution and metabolism of an immunosuppressant drug can vary greatly between patients and because of the wide range and severity of adverse reactions, accurate monitoring of the drug level is essential.

Most whole blood assays for immunosuppressant drugs require a manual step to extract the drug from blood constituents using organic solvents. As a result, the drug molecules are extracted into a relatively clean solution in which plasma proteins and lipoprotein particles as well as most other molecules are removed. Therefore, the binding of assay antibody to the drug occurs in the absence of most endogenous substances in these assays. However, in a homogenous assay where there is no manual extraction or separation of the drug from blood constituents, an antibody for the immunosuppressant drug has to detect the drug in the presence of most or all blood constituents, which might interfere the binding of the antibody to the immunosuppressant drug and/or its analog.

The present inventors have recognized that hydrophobic drugs, such as immunosuppressant drugs, are absorbed by cholesterol-rich lipoprotein particles (such as low density lipoprotein (LDL) and high density lipoprotein (HDL), etc. The drug is absorbed in such a way that a portion or all of the drug becomes inaccessible to the detection antibody in an assay for the drug, resulting in a decrease in the amount of detectable drug in the assay. Because hyperlipidemia is common in transplant patients, an assay for the determination of an immunosuppressant drug needs to be robust to lipoprotein interference.

There is, therefore, a continuing need to develop fast and accurate diagnostic methods to measure levels of immunosuppressant drugs or derivatives thereof in patients. The methods should be fully automated and be accurate even when conducted on whole blood samples with no-extraction using a homogenous assay where an antibody employed in the assay has to detect the drug in the presence of most, if not all, blood constituents.

SUMMARY

One embodiment of the present invention is a method for enhancing the bioavailability of a hydrophobic drug in a sample suspected of containing a hydrophobic drug. A medium is provided, which comprises in combination the sample and a bioavailability agent for the hydrophobic drug, wherein the bioavailability agent comprises an ionic detergent comprising a chain of at least 10 carbon atoms or a non-ionic detergent comprising a chain of at least 15 repeating ethylene oxide units or propylene oxide units or a combination of ethylene oxide units and propylene oxide units. The concentration of the bioavailability agent in the medium is sufficient to enhance the bioavailability of the hydrophobic drug. The medium is incubated under conditions for enhancing the bioavailability of the hydrophobic drug.

Another embodiment of the present invention is a method for determining a hydrophobic drug in a sample suspected of containing a hydrophobic drug. A combination is formed in a medium where the combination comprises the sample, a hemolytic agent, and a bioavailability agent for the hydrophobic drug. The bioavailability agent comprises an ionic detergent comprising a chain of at least 10 carbon atoms or a non-ionic detergent comprising a chain of at least 15 repeating ethylene oxide units or propylene oxide units or a combination of ethylene oxide units and propylene oxide units. The concentration of the bioavailability agent in the medium is sufficient to enhance the bioavailability of the hydrophobic drug. The medium is incubated under conditions for hemolyzing cells in the sample and for enhancing the bioavailability of the hydrophobic drug. To the medium are added reagents for determining the presence and/or amount of the hydrophobic drug in the sample wherein the reagents comprise at least one antibody for the hydrophobic drug. The medium is examined for the presence of a complex comprising the hydrophobic drug and the antibody for the hydrophobic drug. The presence and/or amount of the complex indicates the presence and/or amount of the hydrophobic drug in the sample.

Another embodiment of the present invention is a method for determining an immunosuppressant drug in a sample suspected of containing an immunosuppressant drug. A combination is formed in a medium wherein the combination comprises the sample, a hemolytic agent and a bioavailability agent for the hydrophobic drug as described above. The medium is incubated under conditions for hemolyzing cells in the sample and for enhancing the bioavailability of the hydrophobic drug. Magnetic particles comprising the immunosuppressant drug or an analog thereof and an antibody for the immunosuppressant drug comprising an enzyme are combined in the medium, which is then examined for the presence of a complex comprising the immunosuppressant drug and the antibody for the immunosuppressant drug. The presence and/or amount of the complex indicates the presence and/or amount of the immunosuppressant drug in the sample.

Another embodiment of the present invention is a method for determining an immunosuppressant drug in a sample suspected of containing an immunosuppressant drug. A combination is formed in a medium wherein the combination comprises the sample, a hemolytic agent and a bioavailability agent for the hydrophobic drug as described above. The medium is incubated under conditions for hemolyzing cells in the sample and for enhancing the bioavailability of the hydrophobic drug. To the medium are added (i) a photosensitizer associated with a first particle and being capable of generating singlet oxygen, and (ii) a chemiluminescent composition activatable by singlet oxygen and associated with a second particle. The first particle or the second particle, or both, comprise an antibody for the immunosuppressant drug. The combination is subjected to conditions for binding of the antibody to the immunosuppressant drug, if present. The photosensitizer is irradiated with light and the amount of luminescence generated by the chemiluminescent composition is detected. The amount of luminescence is related to the amount of the immunosuppressant drug in the sample.

Alternatively, in the above embodiment, one of the first particle or the second particle comprises the antibody and the other particle comprises a drug analog for the immunosuppressant drug. The combination is subjected to conditions for competition of the drug analog coated particles and the immunosuppressant drug, if present, to the antibody for the drug. Alternatively, in the above embodiment, the first particle or the second particle comprises streptavidin, which combines with a biotinylated analog for the immunosuppressant drug in the medium. The combination is subjected to conditions for competition of biotinylated drug analog and the immunosuppressant drug for the antibody for the drug. In either of the above alternative embodiments, the photosensitizer is irradiated with light and the amount of luminescence generated by the chemiluminescent composition is detected. The amount of luminescence is related to the amount of the immunosuppressant drug in the sample.

DETAILED DESCRIPTION OF SPECIFIC EMBODIMENTS

General Discussion

The current methods focus on the mitigation of interference caused by endogenous blood constituents, especially by lipoproteins and in particular triglycerides and cholesterol. The present methods have application to fully automated homogenous assays in which, prior to the assay, there is no extraction or separation of the hydrophobic drug from other constituents of the sample such as, for example, blood constituents that may include lipoproteins. In a "non-manual extraction" assay, a sample such as a whole blood sample is combined with a hemolyzing agent in a medium and, following an incubation period to allow for hemolysis, reagents for conducting an assay for the hydrophobic drug are added to the medium and the assay is conducted. It has been found that the bioavailability of a hydrophobic drug in an assay for the drug may be enhanced by incubating a sample suspected of containing the hydrophobic drug with a bioavailability agent that enhances the availability of the hydrophobic drug for subsequent binding to an antibody for the drug during an assay to detect the presence and/or amount of the drug wherein other constituents of the sample are present.

The term "hydrophobic drug" as used herein refers to a drug, usually a therapeutic drug, where the drug exhibits a characteristic of absorption by a lipoprotein to an extent that the absorption interferes with the quantitation of the drug in an assay for the drug. Interference with the quantitation of the drug means that the ability to make an accurate quantitative determination of the drug in an assay is reduced by at least about 10%, by at least about 15%, by at least about 20%, by at least about 25%, by at least about 30%, and so forth.

The lipoproteins are spherical particles consisting of a nonpolar lipid core surrounded by a surface monolayer of amphipathic lipids (phospholipids and unesterified cholesterol) and specific proteins called apolipoproteins. A number of different phospholipids are incorporated into the coat of the lipoprotein, the more common of which are phosphatidylcholine, phosphatidylserine, phosphatidylethanolamine, and sphingomyelin. Traditionally, plasma lipoproteins are classified and separated according to their density and are divided into five main categories: chylomicrons, very low density lipoproteins (VLDL), intermediate-density lipoproteins (IDL), low-density lipoproteins (LDL), and high-density lipoproteins (HDL). For effective mitigation of interference from lipoproteins in accordance with the present methods, a bioavailability agent should mitigate or substantially reduce both triglyceride and cholesterol interference.

Immunosuppressant drugs are an example of hydrophobic drugs. Immunosuppressant drugs are therapeutic drugs that are administered to transplant recipients in order to help prevent allograft rejection of non-self tissue. Immunosuppressive drugs can be classified into four groups: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance Two distinct families of immunophilins are presently known: cyclophilins and macrophilins, the latter of which specifically bind, for example, tacrolimus or sirolimus. The immunosuppressant drugs that act on immunophilin include, for example, cyclosporin (including cyclosporin A, cyclosporin B, cyclosporin C, cyclosporin D, cyclosporin E, cyclosporin F, cyclosporin G, cyclosporin H, cyclosporin I), tacrolimus (FK506, PROGRAF®), sirolimus (rapamycin, RAPAMUNE®), everolimus (RAD, CERTICAN®) and so forth.

The term "bioavailability" as used herein refers to the amount of hydrophobic drug in a sample that is available for measurement such as, for example, available for binding to an antibody for the hydrophobic drug particularly in an assay where there are constituents in the sample to be analyzed that absorb the hydrophobic drug, thereby making the hydrophobic drug unavailable for binding to an antibody for the hydrophobic drug. A primary factor affecting bioavailability of concern in the present methods is the absorption of a hydrophobic drug by lipoproteins in a sample to be analyzed where there is no separation of such lipoproteins prior to an assay.

In accordance with the present embodiments, "enhanced bioavailability" or "enhancement of bioavailability" or "enhance the bioavailability" of a hydrophobic drug means that there is an enhancement or increase in the amount of the hydrophobic drug available for detection in a sample that contains increased amounts of cholesterol and triglyceride.

Accordingly, as mentioned above, an embodiment of the present invention is a method for determining a hydrophobic drug in a sample suspected of containing a hydrophobic drug. A combination is formed in a medium where the combination comprises the sample, a hemolytic agent, and a bioavailability agent for the hydrophobic drug. The bioavailability agent comprises an ionic detergent comprising a chain of at least 10 carbon atoms or a non-ionic detergent comprising a chain of at least 15 repeating ethylene oxide units or propylene oxide units and wherein the concentration of the bioavailability agent in the medium is sufficient to render the hydrophobic drug bioavailable. The medium is incubated under conditions for hemolyzing cells in the sample and for rendering the hydrophobic drug bioavailable. To the medium are added reagents for determining the presence and/or amount of the hydrophobic drug in the sample wherein the reagents comprise at least one antibody for the hydrophobic drug. The medium is examined for the presence of a complex comprising the hydrophobic drug and the antibody for the hydrophobic drug. The presence and/or amount of the complex indicate the presence and/or amount of the hydrophobic drug in the sample.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The sample to be analyzed is one that is suspected of containing one or more hydrophobic drug analytes. The sample typically comprises one or more compounds that absorb a hydrophobic drug such as a lipoprotein, particularly, cholesterol and triglyceride. The samples are preferably from humans or animals and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum and, in a particular embodiment the sample is whole blood.

The sample can be prepared in any convenient medium that does not interfere with an assay; an aqueous medium is preferred. The nature of the medium is discussed in more detail below. A hemolytic agent and a bioavailability agent for the hydrophobic drug in accordance with the present methods are combined in the medium.

Hemolytic Agent

A hemolytic agent is a compound or mixture of compounds that disrupt the integrity of the membranes of red blood cells thereby releasing intracellular contents of the cells. Numerous hemolytic agents are known in the art. Hemolytic agents include, for example, non-ionic detergents, anionic detergents, amphoteric detergents, low ionic strength aqueous solutions (hypotonic solutions), bacterial agents, antibodies that cause complement dependent lysis, and the like. Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis(ethoxylate-block-propoxylate)tetrol, IGEPAL®, MERPOL®, poly(ethylene glycol), 2-[ethyl[(heptadecafluorooctyl)sulfonyl]amino]ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanoliamin, phosphatidyl choline, phosphatidyl inositol, phosphatidylcholine, bile salt, unesterified cholesterol, neutralized sphingosine, ceramide, and the like. Combinations of one or more synthetic detergents or one or more naturally-occurring detergents and combinations of synthetic detergents and naturally-occurring detergents may also be employed.

The nature and amount or concentration of hemolytic agent employed depends on the nature of the sample, the nature of the hydrophobic drug, the nature of the rest of the reagent components, the reaction conditions, and the like. The amount of the hemolytic agent is at least sufficient to cause lysis of red blood cells to release contents of the cells. In some embodiments the amount of the hemolytic agent is about 0.0001% to about 0.5%, about 0.001% to about 0.4%, about 0.01% to about 0.3%, about 0.01% to about 0.2%, about 0.1% to about 0.3%, about 0.2% to about 0.5%, about 0.1% to about 0.2%, and so forth (percent is by volume).

Bioavailability Agent

The bioavailability agent in accordance with embodiments of the present methods comprises an ionic detergent comprising a chain of at least 10 carbon atoms or a non-ionic detergent comprising a chain of at least 15 repeating ethylene oxide units or propylene oxide units or a combination of repeating ethylene oxide and propylene oxide segments wherein the repeating segments comprise ethylene oxide and propylene oxide units, respectively. Combinations comprising one or more of the above-mentioned detergents with other agents and materials are also included within the definition of bioavailability agent. In some embodiments the bioavailability agent is a liquid.

The ionic detergent mentioned above may be anionic or cationic. In many embodiments the ionic detergent is anionic. In some embodiments the ionic detergent comprises a chain of at least about 10, or at least about 11, or at least about 12, or at least about 13, or at least about 14, or at least about 15, or at least about 16, or at least about 17, or at least about 18, or at least about 19, or at least about 20 carbon atoms. The number of carbon atoms in the chain is usually not greater than about 50, or not greater than about 40, or not greater than about 30, and so forth. The chain is usually non-cyclic, i.e., there are no rings as part of the chain. The chain may comprise repeating methylene units such as, for example, —CH$_2$(CH$_2$)$_n$CH$_2$— wherein n is about 8 to about 30, or about 9 to about 30, or about 10 to about 30, or about 11 to about 30, or about 12 to about 30, or about 8 to about 25, or about 8 to about 20, or about 9 to about 25, or about 9 to about 20, or about 10 to about 25, or about 10 to about 20, or about 11 to about 25, or about 11 to about 20, or about 12 to about 25, or about 12 to about 20, and so forth. In some embodiments 1 to 3, or 1 to 2, or 2 to 3, carbon atoms of the chain may be replaced by an oxygen moiety thereby forming an ether.

One or more hydrogens of the methylene chain may be substituted with alkyl of about 1 to about 5, or about 1 to about 4, or about 1 to about 3, or about 1 to about 2, or about 2 to about 5, or about 2 to about 4, or about 2 to about 3, or about 3 to about 5, or about 3 to about 4 carbon atoms. As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, and the like. Other substituents on the methylene chain in place of one or more hydrogens include, for example, keto, amino, phenyl, and the like. In many embodiments the number of substituents on the methylene chain is no greater than 3, or no greater than 2 or no greater than 1. One terminus of the methylene chain may be methyl, alkyl phenol, and the like. The other terminus of the methylene chain may be an anionic substituent or a cationic substituent depending on whether the detergent is anionic or cationic. In some embodiments the terminus may be a sulfate ion, sulfite ion, carboxylate ion, phosphate ion, phosphite ion, amine oxide (secondary or tertiary), ammonium ion (primary, secondary or tertiary), and so forth.

In some embodiments the bioavailability agent comprises a chain of at least 12 or 13 or 14 or 15 or 16 carbon atoms, for example, $CH_3(CH_2)_nCH_2$— wherein n is 10, 11, 12, 13 or 14. In some embodiments the terminus of the chain, other than the terminus that comprises the terminal methyl group, is an anion moiety such as, for example, a sulfate ion, with no internal ionic moiety; in some embodiments the terminus of the chain, other than the terminus that comprises the terminal methyl group, is a cationic moiety such as, for example, an ammonium ion, with no internal ionic moiety. In some embodiments the alpha carbon comprises a substituent such as, for example, a keto group. In particular embodiments the bioavailability agent is an alkyl sulfate wherein alkyl comprises a chain of 12 to 16 carbon atoms. Examples of such embodiments the bioavailability agent include the detergents sodium dodecylsulfate (duponol, duponal WAQE), lithium dodecylsulfate, and the like. In many embodiments the bioavailability agent is not zwitterionic.

As mentioned above, the bioavailability agent may be a non-ionic detergent comprising a chain of at least 15 repeating ethylene oxide units or propylene oxide units or a combination of ethylene oxide and propylene oxide units. In some embodiments the chain is linear as opposed to branched. In some embodiments the non-ionic detergent comprises a chain of at least about 15, or at least about 16, or at least about 17, or at least about 18, or at least about 19, or at least about 20, or at least about 21, or at least about 22, or at least about 23, or at least about 24, or at least about 25, or at least about 26, or at least about 27, or at least about 28, or at least about 29, or at least about 30, or at least about 31, or at least about 32, or at least about 33, or at least about 34, or at least about 35 repeating units as mentioned above. The number of repeating units in the chain is usually not greater than about 50, or not greater than about 45, or not greater than about 40, and so forth. When the chain comprises a combination of repeating ethylene oxide units and propylene oxide units, the ratio of ethylene oxide units to propylene oxide units is about 1:1, or about 2:1, or about 3:1, or about 1:2, or about 1:3, or about 1:4, or about 1:5, or about 1:6, or about 1:7, or about 1:8, and the like. In the above embodiments the repeating ethylene oxide units and propylene oxide units may alternate. Each repeating ethylene oxide unit may be a segment of ethylene oxide units where the segments have the same length or different lengths, i.e., may comprise the same number of ethylene oxide units or a different number of ethylene oxide units. Each repeating propylene oxide unit may be a segment of propylene oxide units where the segments have the same length or different lengths, i.e., may comprise the same number of propylene oxide units or a different number of propylene oxide units. For example, in some embodiments the detergent comprises terminal ethylene oxide segments comprising about 1 to about 5, or about 1 to about 4, or about 1 to about 3, or about 1 to about 2, or about 2 to about 5, or about 2 to about 4, or about 2 to about 3, or about 3 to about 5, or about 4 to about 5 ethylene oxide units and an internal propylene oxide segment comprising about 10 to about 30, or about 10 to about 25, or about 10 to about 20, or about 15 to about 30, or about 15 to about 25, or about 15 to about 20, or about 20 to about 30, or about 20 to about 25 propylene oxide units.

In some embodiments the chain may comprise repeating ethylene oxide units such as, for example, —$(CH_2CH_2O)_p$— wherein p is about 15 to about 40, or about 20 to about 40, or about 25 to about 40, or about 15 to about 35, or about 20 to about 35, or about 25 to about 35, or about 30 to about 35, and so forth. In some embodiments the chain may comprise repeating propylene oxide units such as, for example, —$(CH_2CH(CH_3)O)_q$— wherein q is about 15 to about 30, or about 20 to about 30, or about 25 to about 30, or about 15 to about 25, or about 20 to about 25, or about 25 to about 35, or about 30 to about 35, and so forth.

In some embodiments the chain may comprise a combination of ethylene oxide units and propylene units such as, for example, —$(CH_2CH_2O)_s$—$(CH_2CH(CH_3)O)_t$— wherein (s+t) is at least about 15, or at least about 16, or at least about 17, or at least about 18, or at least about 19, or at least about 20, or at least about 21, or at least about 22, or at least about 23, or at least about 24, or at least about 25 carbon atoms, or at least about 26, or at least about 27, or at least about 28, or at least about 29, or at least about 30, or at least about 31, or at least about 32, or at least about 33, or at least about 34, or at least about 35 and usually no more than about 40, no more than about 39, no more than about 38, no more than about 37, no more than about 36. In some embodiments (s+t) is about 15 to about 40, or about 20 to about 40, or about 25 to about 40, or about 15 to about 35, or about 20 to about 35, or about 25 to about 35, or about 30 to about 35, about 15 to about 30, or about 20 to about 30, or about 25 to about 30, or about 15 to about 25, and so forth. In some embodiments, as long as (s+t) is as defined above, s is about 1 to about 30, or about 1 to about 25, or about 1 to about 20, or about 1 to about 15, or about 1 to about 10, or about 1 to about 5, or about 2 to about 30, or about 2 to about 25, or about 2 to about 20, or about 2 to about 15, 5 to about 30, or about 5 to about 25, or about 5 to about 20, or about 5 to about 15, or about 5 to about 10, or about 10 to about 30, or about 10 to about 25, or about 10 to about 20, or about 10 to about 15, or about 15 to about 30, or about 15 to about 25, or about 15 to about 20, or about 20 to about 30, or about 20 to about 25, or about 25 to about 30, and t is about 5 to about 30, or about 5 to about 25, or about 5 to about 20, or about 5 to about 15, or about 5 to about 10, or about 10 to about 30, or about 10 to about 25, or about 10 to about 20, or about 10 to about 15, or about 15 to about 30, or about 15 to about 25, or about 15 to about 20, or about 20 to about 30, or about 20 to about 25, or about 25 to about 30.

One or more hydrogens of the chain may be substituted with alkyl of about 1 to about 5, or about 1 to about 4, or about 1 to about 3, or about 1 to about 2, or about 2 to about 5, or about 2 to about 4, or about 2 to about 3, or about 3 to about 5, or about 3 to about 4 carbon atoms, sometimes referred to herein as lower alkyl. Other substituents on the chain in place of one or more hydrogens include, for example, keto, amino, alkyl phenol, and the like. In many embodiments the number of substituents on the chain is no greater than 3, or no greater than 2 or no greater than 1. In some embodiments one terminus of the chain may be methyl, hydroxyl, phenyl, and the like. In some embodiments the other terminus of the chain may be methyl, hydroxyl, phenyl, and the like.

In some embodiments the bioavailability agent comprises a chain of at least about 30 or 31 or 32 or 33 or 34 or 35 repeating ethylene oxide units, for example, —$(CH_2CH_2O)_p$— wherein p is 30, 31, 32, 33, 34 or 35. In some embodiments both ends of the chain are hydroxyl. Particular examples of embodiments of the bioavailability agent comprising repeating ethylene oxide units are those comprising a chain of 30 or 35 repeating ethylene oxide units wherein both ends of the chain are hydroxy. Specific examples of embodiments of the bioavailability agents include the detergents TRITON™ X-405, TRITON™ SP-135, and the like.

In some embodiments the bioavailability agent comprises a chain comprising a combination of about 1 to about 20, or about 1 to about 15, or about 1 to about 10, or about 1 to about 5, or about 2 to about 20, or about 2 to about 15, or about 2 to about 10, or about 2 to about 5, about 3 to about 20, or about 3 to about 15, or about 3 to about 10, or about 3 to about 5, about 4 to about 20, or about 4 to about 15, or about 4 to about 10, or about 4 to about 5, about 5 to about 20, or about 5 to about 15, or about 5 to about 10, ethylene oxide units and about 5 to about 50 or about 5 to about 40, or about 5 to about 30, or about 5 to about 20, or about 5 to about 10, or about 10 to about 50, or about 10 to about 40, or about 10 to about 30, or about 10 to about 20, or about 15 to about 50, or about 15 to about 40, or about 15 to about 30, about 15 to about 20, or about 20 to about 50, or about 20 to about 40, or about 20 to about 30, about 20 to about 25, or about 25 to about 50, or about 25 to about 40, or about 25 to about 30, or about 30 to about 50, or about 30 to about 40, or about 30 to about 35, or about 35 to about 50, or about 35 to about 40, or about 40 to about 50, propylene oxide units. In some embodiments both ends of the chain are hydroxyl.

In some embodiments the chain may comprise a combination of ethylene oxide units and propylene oxide units such as, for example, $-(CH_2CH_2O)_s-(CH_2CH(CH_3)O)_t-(CH_2CH_2O)_s-$ wherein each s is 1 to 3 or 1 to 2 and wherein t is 15 to 40 or 15 to 35 or 15 to 30 and wherein each terminus of the chain is hydroxyl. Particular examples of embodiments of the bioavailability agent comprising such a combination of ethylene oxide units and propylene oxide units include the detergents PLURONIC® 25R2, PLURONIC® 25R1, PLURONIC® 25R4, PLURONIC® 31R1, PLURONIC® 31R2, PLURONIC® 17R1, PLURONIC® 17R2, PLURONIC® 10R5, PLURONIC® L123, PLURONIC® L31, and the like. Other examples of embodiments of the bioavailability agent comprising such a combination of ethylene oxide units and propylene oxide units include the detergents DOWFAX® 63N10, DOWFAX® 63N13, DOWFAX® 63N30, DOWFAX® 63N40, DOWFAX® 20A612, DOWFAX® DF101, DOWFAX® DF111, DOWFAX® DF112, and the like.

As mentioned above, the bioavailability agents in accordance with embodiments of the present invention mitigate interference from both cholesterol and triglycerides on the availability of a hydrophobic drug for binding to an antibody in an assay for the hydrophobic drug. The bioavailability agent may be a combination of one or more of the above compounds either in combination with another of such compounds or in combination with one or more other compounds that may have a sufficient mitigating effect on either cholesterol interference or triglyceride interference but not both. Such compounds include, for example, the detergents saponin, GAFAC®, TWEEN® 20, TWEEN® 80, EP110™, ZWITTERGENT® (zwitterionic amidosulfobetaine detergents such as, for example, 3-(N,N-dimethyltetradecylammonio)propanesulfonate), TRITON™ X-100, bile salt, certain PLURONIC® and DOWFAX® detergents, and the like. It should be noted that the bioavailability agents in accordance with embodiments of the present invention are effective in mitigating interference from both triglycerides and cholesterol in the absence of the aforementioned compounds.

The concentration of the bioavailability agent in the medium is sufficient to achieve enhanced bioavailability of the hydrophobic drug, i.e., to reduce interference or absorption by lipoproteins, particularly cholesterol and triglycerides, in a sample such that an accurate quantitation of the hydrophobic drug may be realized in an automated homogeneous assay for the hydrophobic drug. In other words, the concentration of the bioavailability agent in the medium is sufficient such that the amount of the hydrophobic drug in the sample that is available for binding to a specific binding member for the hydrophobic drug is sufficient for an accurate determination of the amount of hydrophobic drug in the sample. Accordingly, the concentration or amount of the bioavailability agent should be sufficient to mitigate or reduce interference from lipoproteins, particularly both triglycerides and cholesterol, thus achieving an enhancement in the amount of hydrophobic drug available for detection in an assay.

For cholesterol, interference is sufficiently reduced, and the bioavailability of the hydrophobic drug is enhanced, thereby enhancing the accuracy of its detection, when the amount of hydrophobic drug that is detectable in a high cholesterol sample (e.g., 400 mg/dL) is increased over that obtained in the absence of the bioavailability agent by at least about 50%, by at least about 55%, by at least about 60%, by at least about 65%, by at least about 70%, by at least about 75%, by at least about 80%, by at least about 85%, by at least about 90%, by at least about 95%, by at least about 100%, by at least about 105%, by at least about 110%, by at least about 115%, by at least about 120%, by at least about 125%, by at least about 130%, by at least about 135%, by at least about 140%, by at least about 145%, by at least about 150%, by at least about 155%, by at least about 160%, by at least about 165%, and so forth.

For triglyceride, interference is sufficiently reduced, and the bioavailability of the hydrophobic drug is enhanced, thereby enhancing the accuracy of its detection, when the amount of hydrophobic drug that is detectable in a high triglyceride sample (e.g., 1000 mg/dL) is increased over that obtained in the absence of the bioavailability agent by at least about 40%, by at least about 45%, by at least about 50%, by at least about 55%, by at least about 60%, by at least about 65%, by at least about 70%, by at least about 75%, by at least about 80%, by at least about 85%, by at least about 90%, by at least about 95%, by at least about 100%, and so forth. As discussed in more detail below, the above parameters for enhanced bioavailability may be evaluated using an ACMIA assay on the DIMENSION® clinical chemistry analyzer where a sample high in cholesterol contains about 400 mg/dL and a sample high in triglyceride contains about 1000 mg/dL.

The amount or concentration of bioavailability agent employed depends on the nature of the sample, the nature of the hydrophobic drug, the presence of other detergent compounds and organic solvents, the nature of other reagent components, the reaction conditions and the like. In some embodiments the amount of the bioavailability agent is about 0.0001% to about 0.5%, about 0.001% to about 0.4%, about 0.01% to about 0.3%, about 0.01% to about 0.2%, about 0.1% to about 0.3%, about 0.2% to about 0.5%, about 0.1% to about 0.2%, and so forth (percent is by volume). In some embodiments the maximum concentration of bioavailability agent is less than the critical micelle concentration for those detergents exhibiting such a characteristic, such as, for example, the detergents TRITON™ X-405, sodium dodecylsulfate, lithium dodecylsulfate, and the like. In some embodiments the maximum concentration of bioavailability agent is less than the aggregation concentration range or the limiting aggregation concentration for those detergents exhibiting such a characteristic, such as, for example, the detergents PLURONIC® 25R2, PLURONIC® 25R1, PLURONIC® 25R4, PLURONIC® 31R1, PLURONIC® 31R2, PLURONIC® 17R1, PLURONIC® 17R2, PLURONIC® 10R5, PLURONIC® L123, PLURONIC® L31, and the like.

Hemolysis and Enhancement of Bioavailability

The sample, the hemolytic agent and the bioavailability agent are combined in a medium, which, as mentioned above, is usually an aqueous medium. All of the above may be combined simultaneously in the medium or one or more of the above reagents may be added sequentially. The aqueous medium may be solely water or may include from 0.1 to about 40 volume percent of a cosolvent such as, for example, an organic solvent, which may be an alcohol, ether, ester, and the like. The medium may also comprise one or more preservatives as are known in the art such as, for example, sodium azide, neomycin sulfate, PROCLIN® 300, Streptomycin, and the like. The pH for the medium will usually be in the range of about 4 to about 11, more usually in the range of about 5 to about 10, and preferably in the range of about 6.5 to about 9.5.

Various buffers may be used to achieve the desired pH and maintain the pH during the incubation period. Illustrative buffers include borate, phosphate, carbonate, tris, barbital, PIPES, HEPES, MES, ACES, MOPS, BICINE, and the like. The medium may also comprise agents for preventing the formation of blood clots. Such agents are well known in the art and include, for example, EDTA, EGTA, citrate, heparin, and the like. Various ancillary materials may be employed in the above methods. For example, in addition to buffers and preservatives, the medium may comprise stabilizers for the medium and for the reagents employed. The medium may comprise an agent for mitigating the effect of binding proteins in the sample where the binding proteins bind to the hydrophobic drug. Such agents may be, for example, an ester of the hydrophobic drug to be determined. For example, in a determination for tacrolimus, an ester of tacrolimus may be included in the medium. All of the above materials are present in a concentration or amount sufficient to achieve the desired effect or function.

The medium is incubated under conditions for hemolyzing cells in the sample and for enhancing the bioavailability of the hydrophobic drug. The incubation period may be about 1 second to about 60 minutes, or about 1 second to about 6 minutes, or about 1 second to about 5 minutes, or about 1 second to about 3 minutes, or about 1 second to about 2 minutes, or about 1 second to about 1 minute, or about 1 second to about 30 seconds, or about 1 second to about 20 seconds, or about 1 second to about 10 seconds, or about 5 seconds to about 60 minutes, or about 5 seconds to about 6 minutes, or about 5 seconds to about 5 minutes, or about 5 seconds to about 3 minutes, or about 5 seconds to about 2 minutes, or about 5 seconds to about 1 minute, or about 5 seconds to about 30 seconds, or about 5 seconds to about 20 seconds, or about 5 seconds to about 10 seconds, or about 10 seconds to about 60 minutes, or about 10 seconds to about 6 minutes, or about 10 seconds to about 5 minutes, or about 10 seconds to about 3 minutes, or about 10 seconds to about 2 minutes, or about 10 seconds to about 1 minute, or about 10 seconds to about 30 seconds, or about 10 seconds to about 20 seconds, or about 20 seconds to about 60 minutes, or about 20 seconds to about 6 minutes, or about 20 seconds to about 5 minutes, or about 20 seconds to about 3 minutes, or about 20 seconds to about 2 minutes, or about 20 seconds to about 1 minute, or about 20 seconds to about 30 seconds, or about 30 seconds to about 60 minutes, or about 30 seconds to about 6 minutes, or about 30 seconds to about 5 minutes, or about 30 seconds to about 3 minutes, or about 30 seconds to about 2 minutes, or about 30 seconds to about 1 minute, or about 1 minute to about 30 minutes, or about 1 minute to about 20 minutes, or about 1 minute to about 10 minutes, or the like.

The temperature during the incubation is usually about 10° C. to about 45° C., or about 10° C. to about 35° C., or about 10° C. to about 25° C., or about 15° C. to about 45° C., or about 15° C. to about 35° C., or about 15° C. to about 25° C., or about 20° C. to about 45° C., or about 20° C. to about 35° C., or about 20° C. to about 25° C., or the like.

General Description of Assays for a Hydrophobic Drug

Following the above incubation period, reagents for determining the presence and/or amount of the hydrophobic drug in the sample are added to the medium. The nature of the reagents is dependent on the particular type of assay to be performed. In general, the assay is a method for the determination or measuring of the presence and/or amount of a hydrophobic analyte. Various assay methods are discussed below by way of illustration and not limitation.

In many embodiments the reagents comprise at least one antibody for the hydrophobic drug. By the phrase "antibody for the hydrophobic drug" is meant an antibody that binds specifically to the hydrophobic drug and does not bind to any significant degree to other substances that would distort the analysis for the hydrophobic drug.

Antibodies specific for a hydrophobic drug for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1-24 (1975); Broughton and Strong, Clin. Chem. 22: 726-732 (1976); and Playfair, et al., Br. Med. Bull. 30: 24-31 (1974).

Antibodies can also be obtained by somatic cell hybridization techniques, such antibodies being commonly referred to as monoclonal antibodies. Monoclonal antibodies may be produced according to the standard techniques of Köhler and Milstein, Nature 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites.

As discussed above, an antibody selected for use in an immunoassay for a hydrophobic drug, for example, should specifically and preferentially bind the hydrophobic drug and its pharmaceutically active metabolites over other ligands such as other metabolites or related drugs. For example, an antibody for tacrolimus should specifically and preferentially bind tacrolimus over, e.g., rapamycin. In general, an antibody should be capable of distinguishing between one hydrophobic drug relative to a second hydrophobic drug. At least about 5-fold, at least about 10-fold, or at least about 20-fold, of the first hydrophobic drug will be bound to the antibody if the antibody is combined with a sample containing the hydrophobic drug. While the binding also depends on relative concentration of the hydrophobic drug, the binding will be higher for the first hydrophobic drug if the binding constant for the first hydrophobic drug is greater than the binding constant for the second hydrophobic drug, at least about 10-fold higher or at least about 50-fold higher and up to 1000-fold or higher.

Other reagents are included in the assay medium depending on the nature of the assay to be conducted. Such assays usually involve reactions between binding partners such as a hydrophobic drug analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

Many types of immunoassays may be employed in the present methods to determine the presence and/or amount of a hydrophobic drug analyte in a sample suspected of containing such analytes. The immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include enzyme immunoassays, fluorescence polarization immunoassays, radioimmunoassay, inhibition assay, induced luminescence, fluorescent oxygen channeling assay, and so forth.

In many of the assays discussed herein, a label is employed; the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the hydrophobic drug being detected or to an agent that reflects the amount of the hydrophobic drug to be detected. The label is any molecule that produces or can be induced to produce a signal, and may be, for example, a fluorescer, radiolabel, enzyme, chemiluminescer or photosensitizer. Thus, the signal is detected and/or measured by detecting enzyme activity, luminescence, light absorbance or radioactivity, and so forth, as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chrome particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members can be bound to a support. A hydrophobic drug derivative or analog may be bound to a solid support in any manner known in the art, provided only that the binding does not substantially interfere with the analogs ability to bind with an antibody. In some embodiments, the hydrophobic drug derivative or analog may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the hydrophobic drug. Other methods of binding the hydrophobic drug derivatives are also possible. For instance, a solid support may have a coating of a binder for a small molecule such as, for example, avidin, an antibody, etc., and a small molecule such as, e.g., biotin, hapten, etc., can be bound to the hydrophobic drug derivative or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, DENDRIMERS, and the like. Depending on the type of assay, the support may or may not be suspendable in the medium in which it is employed. Examples of suspendable supports are polymeric materials such as latex, lipid bilayers or liposomes, oil droplets, cells and hydrogels, magnetic particles, and the like. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chrome particles or latex particles.

The polymer particles can be formed of addition or condensation polymers. The particles will be readily dispersible in an aqueous medium and can be adsorptive or functionalizable so as to permit conjugation to a hydrophobic drug analog, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The label and/or other sps member may be bound to an sbp member or another molecule. For example, the label can be bound covalently to an sbp member such as, for example, an antibody; a receptor for an antibody, a receptor that is capable of binding to a small molecule conjugated to an antibody, or a ligand analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

With label proteins such as, for example, enzymes, the molecular weight range will be from about 10,000 to about 600,000, or from about 10,000 to about 300,000 molecular weight. There is usually at least about 1 hydrophobic drug analog per about 200,000 molecular weight, or at least about 1 per about 150,000 molecular weight, or at least about 1 per about 100,000 molecular weight, or at least about 1 per about 50,000 molecular weight, and so forth. In the case of enzymes, the number of hydrophobic drug analog groups is usually from 1 to about 20, about 2 to about 15, about 3 to about 12, or about 6 to about 10.

The term "non-poly(amino acid) labels" includes those labels that are not proteins (e.g., enzymes). The non-poly (amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the non-poly(amino acid) label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle or the like, metal sol, crystallite, liposome, cell, etc., which may or may not be further labeled with a dye, catalyst or other detectable group, and the like.

One general group of immunoassays that may be employed includes immunoassays using a limited concentration of antibody. Another group of immunoassays involves the use of an excess of one or more of the principal reagents such as, for example, an excess of an antibody for the immunosuppressant drug. Another group of immunoassays are separation-free homogeneous assays in which the labeled reagents modulate the label signal upon hydrophobic drug-antibody binding reactions. Another group of assays includes labeled antibody reagent limited competitive assays for hydrophobic drug that avoid the use of problematic labeled haptens. In this type of assay, the solid phase immobilized hydrophobic drug analyte is present in a constant, limited amount. The partition of a label between the immobilized hydrophobic drug analyte and free hydrophobic drug analyte depends on the concentration of analyte in the sample.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of an antibody-immobilized surface upon the binding of a hydrophobic drug. Such assays include, for example, optical immunosensor assays, acoustic immunosensor assays, semiconductor immunosensor assays, electrochemical transducer immunosensor assays, potentiometric immunosensor assays, amperometric electrode assays, and the like.

In some embodiments of assays that may be used in the present methods, an analog of the hydrophobic drug is added to the medium. A hydrophobic drug analog is a modified drug that can compete with the analogous hydrophobic drug for a receptor, the modification providing means to join a hydrophobic drug analog to another molecule. The hydrophobic drug analog will usually differ from the hydrophobic drug by more than replacement of a hydrogen with a bond which links the drug analog to a hub or label, but need not. The hydrophobic drug analog binds to the receptor in a manner similar to the binding of hydrophobic drug to the receptor. The hydrophobic drug analog may be, for example, the hydrophobic drug conjugated to another molecule through a linking group, an antibody directed against the idiotype of an antibody to the hydrophobic drug, and so forth.

In one embodiment the assay is an induced luminescence immunoassay, which is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member, for example, an antibody for the hydrophobic drug that is capable of binding to the hydrophobic drug analyte to form a complex, or to a second sbp member to form a complex, in relation to the presence of the hydrophobic drug analyte. If the hydrophobic drug analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of hydrophobic drug analyte present.

By way of further illustration, chemiluminescent particles are employed, which comprise the chemiluminescent compound associated therewith such as by incorporation therein or attachment thereto. An sbp member that binds to the hydrophobic drug analyte, such as, for example, an antibody for a hydrophobic drug, is bound to a polysaccharide coating the particles. A second sbp member that binds to the hydrophobic drug analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with a sample suspected of containing a hydrophobic drug analyte and the photosensitizer particles. The reaction medium is incubated to allow the particles to bind to the hydrophobic drug analyte by virtue of the binding of the sbp members to the hydrophobic drug analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the hydrophobic drug analyte, it is activated by singlet oxygen and emits luminescence. The medium is then examined for the presence and/or the amount of luminescence or light emitted, the presence thereof being related to the presence and/or amount of the hydrophobic drug analyte.

Another particular example of an assay that may be employed for the determination of a hydrophobic drug analyte is discussed in U.S. Pat. No. 5,616,719 (Davalian, et al.), which describes fluorescent oxygen channeling immunoassays.

In some embodiments multi-analyte immunoassays may be utilized where the hydrophobic drug analyte may be the subject of detection along with one or more other analytes such as other drugs and the like. Such multi-analyte systems are described, for example, in Loor, et al., J. Anal. Toxicol. 12: 299 (1988).

The assays discussed above are normally carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; binding enhancers, e.g., polyalkylene glycols; or the like.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., or from about 15 to about 40° C.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of hydrophobic drug analyte present in the sample), the particular detection technique and the concentration of the analyte normally determine the concentrations of the various reagents.

The concentrations of the various reagents in the assay medium will generally be determined by the concentration range of interest of the hydrophobic drug analyte, the nature of the assay, and the like. However, the final concentration of each of the reagents is normally determined empirically to optimize the sensitivity of the assay over the range. That is, a variation in concentration of hydrophobic drug analyte that is of significance should provide an accurately measurable signal difference. Considerations such as the nature of the signal producing system and the nature of the analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

Examination Step

In a next step of the method in accordance with the present disclosure, the medium is examined for the presence of a complex comprising the hydrophobic drug and the antibody for the hydrophobic drug. The presence and/or amount of the complex indicates the presence and/or amount of the hydrophobic drug in the sample.

The phrase "measuring the amount of a hydrophobic drug analyte" refers to the quantitative, semiquantitative and qualitative determination of the hydrophobic drug analyte. Methods that are quantitative, semiquantitative and qualitative, as well as all other methods for determining the hydrophobic drug analyte, are considered to be methods of measuring the amount of the hydrophobic drug analyte. For example, a method, which merely detects the presence or absence of the hydrophobic drug analyte in a sample suspected of containing the hydrophobic drug analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the hydrophobic drug in the sample. The particular mode of detection depends on the nature of the sps. As discussed above, there are numerous methods by which a label of an sps can produce a signal detectable by external means, desirably by visual examination, and include, for example, electromagnetic radiation, electrochemistry, heat, radioactivity detection, chemical reagents and so forth.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems, addition of a substrate and/or a cofactor may be necessary.

The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the hydrophobic drug compound present in a sample. Temperatures during measurements generally range from about 10° to about 70° C., or from about 20° to about 45° C., or about 20° to about 25° C. In one approach standard curves are formed using known concentrations of the analytes to be screened. As discussed above, calibrators and other controls may also be used.

Specific Embodiments of Assays

The following examples describe specific embodiments of the invention by way of illustration and not limitation and are intended merely to describe, and not to limit, the scope of the invention.

In a homogeneous assay after all of the reagents have been combined, the signal is determined and related to the amount of analyte in the sample. For example, in an EMIT assay for a hydrophobic drug, a sample suspected of containing the hydrophobic drug is combined in an aqueous medium either simultaneously or sequentially with an enzyme conjugate of the hydrophobic drug, i.e., an analog for the hydrophobic drug, and antibody capable of recognizing the hydrophobic drug. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The hydrophobic drug analyte and the moieties of the enzyme conjugate compete for binding sites on the antibody. The enzyme activity in the medium is then determined, usually by spectrophotometric means, and is compared to the enzyme activity determined when calibrators or reference samples are tested in which a known amount of the hydrophobic drug is present. Typically, the calibrators are tested in a manner similar to the testing of the sample suspected of containing the hydrophobic drug analytes. The calibrators typically contain differing, but known, concentrations of the hydrophobic drug analyte to be determined. Preferably, the concentration ranges present in the calibrators span the range of suspected hydrophobic drug analyte concentrations in unknown samples.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using antibodies for the hydrophobic drug and using procedures as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, which disclosure is incorporated herein by reference. In one type of competitive assay, a support, as discussed herein, having antibodies for the hydrophobic drug bound thereto is contacted with a medium containing the sample and appropriate enzyme conjugates of the hydrophobic drug. After separating the support and the medium, the enzyme activity of the support or the medium is determined by conventional techniques and related to the presence and/or amount of the hydrophobic drug in the sample.

In certain embodiments a second enzyme may be employed in addition to the enzyme of the enzyme conjugate. The enzymes of the pair of enzymes are related in that a product of the first enzyme serves as a substrate for the second enzyme.

Another embodiment of an assay format is a capture assay. In this assay format, the antibody for the hydrophobic drug is covalently bound to a magnetic particle. The sample is incubated with these particles to allow the hydrophobic drug in the sample to bind to the antibodies for the hydrophobic drug. Subsequently, an enzyme that has the hydrophobic drug or a derivative of the hydrophobic drug covalently attached is incubated with the magnetic particles. After washing, the amount of enzyme that is bound to the magnetic particles is measured and is inversely related to the presence and/or amount of the hydrophobic drug in the sample.

The following specific assay descriptions are by way of illustration of, and not as a limitation on, the scope of the present invention. Selection of tacrolimus as the hydrophobic drug is also by way of illustration and not limitation as the present invention has general application to detection of hydrophobic drugs in general and immunosuppressant drugs in particular.

In one embodiment, the test sample or a tacrolimus standard is mixed with a tacrolimus conjugate, i.e., an analog of tacrolimus that is attached to biotin. The tacrolimus of the test sample and the analog of tacrolimus are allowed to compete for binding to the antibody for the tacrolimus, which is capable of binding to tacrolimus or the analog of tacrolimus. After rinsing with an appropriate wash buffer, a detection molecule consisting of streptavidin or avidin conjugated to an enzyme, florescent or chemiluminescent molecule or radioactive moiety can be added to the medium, which is then examined for the presence and/or amount of signal. The presence and/or amount of signal is related to the presence and/or amount of tacrolimus.

In one embodiment the assay employed is an induced luminescence assay as described above. The reagents include two latex bead reagents and a biotinylated anti-tacrolimus mouse monoclonal antibody. The first bead reagent is coated with tacrolimus or a tacrolimus analog and contains chemiluminescent dye. The second bead reagent is coated with streptavidin and contains a photosensitizer dye. In a first step, sample suspected of containing tacrolimus is incubated with biotinylated antibody for tacrolimus, which allows tacrolimus from the sample to saturate a fraction of the biotinylated antibody that is directly related to the tacrolimus concentration. In a second step, the first bead reagent is added and leads to the formation of bead/biotinylated antibody immunocomplexes with the non-saturated fraction of the biotinylated antibody. The second bead reagent is then added and binds to the biotin to form bead pair immunocomplexes. When illuminated by light at 680 nm, the second bead reagent converts dissolved oxygen in the reaction solution into the more energetic singlet oxygen form. In the bead pairs, the singlet oxygen diffuses into the first bead reagent thereby triggering a chemiluminescent reaction. The resulting chemiluminescent signal is measured at 612 nm and is an inverse function of the concentration of tacrolimus in the sample. The amount of this signal is related to the presence and or amount of tacrolimus in the sample.

A specific example of another assay format is ACMIA (Affinity Column Mediated Immuno Assay). For the ACMIA assay format, chrome particles, which are coated with tacrolimus or a tacrolimus analog, are employed as a first component. A second component is an antibody for tacrolimus. This antibody, crosslinked to a reporter enzyme (for example, beta-galactosidase), is added to a reaction vessel in an excess amount, i.e., an amount greater than that required to bind all of the analyte that might be present in a sample. The antibody-enzyme conjugate is mixed with a sample suspected of containing tacrolimus to allow the tacrolimus analyte to bind to the antibody. Next, the chrome reagent is added to bind up any excess antibody-enzyme conjugate. Then, a magnet is applied, which pulls all of the chrome and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the presence and/or amount of tacrolimus in the sample.

In a sandwich assay format, a first reagent comprising chrome particles coated with anti-tacrolimus antibodies and a second reagent comprising a second antibody (or binding protein) for the first antibody conjugated to a reporter enzyme are employed. In this format, the sample suspected of containing tacrolimus is incubated with the chrome particles so that all of the tacrolimus, if present in the sample, becomes bound to the chrome particles. The chrome particles are washed, using a magnet to separate the bound analyte from the supernatant. Then, the second reagent, i.e., antibody (or binding protein) conjugated to a reporter enzyme, is incubated with the chrome particles to form a "sandwich". After washing, the amount of enzyme that is bound to the chrome is measured and is related to the presence and/or amount of tacrolimus in the sample.

Another assay format is EMIT® (Enzyme-Mediated Immunoassay Technology). In this assay format, an enzyme conjugate is formed such as, for example, a conjugate of G-6-PDH and a tacrolimus analog. An antibody for tacrolimus is incubated with the enzyme-conjugate and a sample suspected of containing tacrolimus. Antibody for tacrolimus binds to the tacrolimus analyte in the sample instead of binding to the enzyme conjugate, which reduces the amount of inhibition of the enzyme activity that might otherwise occur in the absence of tacrolimus in the sample. In this way, samples with more tacrolimus analyte will yield higher enzyme activity, and samples with no tacrolimus analyte will have the maximum inhibition and the lowest enzyme activity. The amount of reduction of inhibition of enzyme activity is related to the amount of tacrolimus in the sample.

The reagents for conducting a particular assay may be present in a kit useful for conveniently performing an assay for the determination of a hydrophobic drug analyte. In one embodiment a kit comprises in packaged combination an antibody for a hydrophobic drug analyte and other reagents for performing an assay, the nature of which depend upon the particular assay format. The reagents may each be in separate containers or various reagents can be combined in one or more containers depending on the cross-reactivity and stability of the reagents. The kit can further include other separately packaged reagents for conducting an assay such as additional sbp members, ancillary reagents such as an ancillary enzyme substrate, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The following examples further describe the specific embodiments of the invention by way of illustration and not limitation and are intended to describe and not to limit the scope of the invention. Parts and percentages disclosed herein are by volume unless otherwise indicated.

EXAMPLES

Materials

PLURONIC® 25R2 was purchased from BASF Corporation (Wilmington N.C.). All other chemicals were purchased from the Sigma-Aldrich Company (St. Louis Mo.).

Testing was done using the DIMENSION® RxL analyzer, available from Dade Behring Inc., Newark Del. The instrument was employed using ACMIA™ immunoassay technology. The ACMIA assay method is disclosed in U.S. Pat. Nos. 7,186,518, 5,147,529, 5,128,103, 5,158,871, 4,661,408, 5,151,348, 5,302,532, 5,422,284, 5,447,870, 5,434,051, the disclosures of which are incorporated herein in their entirety). In the embodiment of the ACMIA method used herein and discussed in more detail below, competition between tacrolimus analog on chrome particles and tacrolimus (TACR) in patient samples for antibody for tacrolimus conjugated to an enzyme (conjugate) was utilized to determine the amount of tacrolimus in the patient samples. Conjugate that binds to the tacrolimus analog on chrome particles was removed by magnetic separation. The enzymatic activity from conjugate remaining in the supernatant is measured and is directly proportional to the amount of tacrolimus in the patient sample. In the ACMIA assay format employed, the enzymatic activity observed when testing a sample containing no tacrolimus was indicative of the amount of enzymatic activity that was not bound to active antibody (i.e., cannot bind tacrolimus on chrome particles). The enzymatic activity observed when no chrome particle is present is indicative of the total amount of enzymatic activity in the conjugate. These values can be used to estimate the percent of enzymatic activity bound to active antibody.

Example 1

Automated Immunoassay for Hydrophobic Drugs with Reduced Lipid Interference Utilizing a Non-manual Pretreatment Preparation of Pretreatment Solution Containing PLURONIC® 25R2

This pretreatment base solution was prepared by adding PLURONIC® 25R2 to a final concentration of 0.09% into a buffer containing 6.8 mg/mL PIPES™ 1.5 sodium salt, 0.3 mg/mL EDTA Disodium, 1.0 mg/mL Saponin, 5 µg/mL of a FK-506 carbamate compound (or tacrolimus ester), 0.2% Proclin 300, 0.024 mg/mL Neomycin sulfate and 0.99 mg/mL $NaN_3$, pH 6.5. The concentration of PLURONIC® 25R2 in the final reaction mixture was approximately 0.021%.

Preparation of Pretreatment Solution Containing SDS

This pretreatment base solution was prepared by adding Sodium Dodecyl Sulfate (SDS) to a final concentration of 0.2% into a buffer containing 6.8 mg/mL PIPES 1.5 sodium salt, 0.3 mg/mL EDTA Disodium, 1.0 mg/mL Saponin, 5 µg/mL of a FK-506 carbamate compound (or tacrolimus ester), 0.2% Proclin 300, 0.024 mg/mL Neomycin sulfate and 0.99 mg/mL $NaN_3$, pH 6.5. The concentration of SDS in the final ACMIA reaction mixture was approximately 0.047%.

Preparation of Pretreatment Solution Containing LDS

This pretreatment base solution was prepared by adding Lithium Dodecyl Sulfate (LDS) was added to a final concentration of 0.05% into a buffer containing 6.8 mg/mL PIPES 1.5 lithium salt, 0.3 mg/mL EDTA Dilithium, 1.0 mg/mL Saponin, 5 µg/mL of a FK-506 carbamate compound (or tacrolimus ester), 0.2% Proclin 300, 0.024 mg/mL Neomycin sulfate and 0.99 mg/mL $NaN_3$, pH 6.5. The concentration of LDS in the final ACMIA reaction mixture was approximately 0.012%, which is lower than the LDS CMC (0.24%).

Preparation of Pretreatment Solution Containing TRITON™ X405

This pretreatment base solution was prepared by adding TRITON™ X405 was added to a final concentration of 0.5% into a buffer containing 6.8 mg/mL PIPES 1.5 sodium salt, 0.3 mg/mL EDTA Disodium, 1.0 mg/mL Saponin, 5 µg/mL of a FK-506 carbamate compound (or tacrolimus ester), 0.2%

Proclin 300, 0.024 mg/mL Neomycin sulfate and 0.99 mg/mL NaN$_3$, pH 6.5. The concentration of TRITON™ X405 in the final ACMIA reaction mixture is approximately 0.117%.

Preparation of Pretreatment Solution Containing GAFAC®

This pretreatment base solution was prepared by adding GAFAC® was added to a final concentration of 0.2% into a buffer containing 6.8 mg/mL PIPES 1.5 sodium salt, 0.3 mg/mL EDTA Disodium, 1.0 mg/mL Saponin, 5 µg/mL of a FK-506 carbamate compound (or tacrolimus ester), 0.2% Proclin 300, 0.024 mg/mL Neomycin sulfate and 0.99 mg/mL NaN$_3$, pH 6.5. The concentration of GAFAC® in the final ACMIA reaction mixture is approximately 0.047%.

Preparation of Pretreatment Solution Containing EP110®

This pretreatment base solution was prepared by adding EP110® was added to a final concentration of 0.05% into a buffer containing 6.8 mg/mL PIPES 1.5 sodium salt, 0.3 mg/mL EDTA Disodium, 1.0 mg/mL Saponin, 5 µg/mL of a FK-506 carbamate compound (or tacrolimus ester), 0.2% Proclin 300, 0.024 mg/mL Neomycin sulfate and 0.99 mg/mL NaN$_3$, pH 6.5. The concentration of EP110® in the final ACMIA reaction mixture is approximately 0.0117%.

Preparation of Pretreatment Solution Containing ZWITTERGENT®

This pretreatment base solution was prepared by adding ZWITTERGENT® was added to a final concentration of 0.1% into a buffer containing 6.8 mg/mL PIPES 1.5 sodium salt, 0.3 mg/mL EDTA Disodium, 1.0 mg/mL Saponin, 5 µg/mL of a FK-506 carbamate compound (or tacrolimus ester), 0.2% Proclin 300, 0.024 mg/mL Neomycin sulfate and 0.99 mg/mL NaN$_3$, pH 6.5. The concentration of ZWITTERGENT® in the final ACMIA reaction mixture is approximately 0.0234%.

Preparation of Pretreatment Solution Containing TWEEN® 20

This pretreatment base solution was prepared by adding TWEEN® 20 was added to a final concentration of 0.1% into a buffer containing 6.8 mg/mL PIPES 1.5 sodium salt, 0.3 mg/mL EDTA Disodium, 1.0 mg/mL Saponin, 5 µg/mL of a FK-506 carbamate compound (or tacrolimus ester), 0.2% Proclin 300, 0.024 mg/mL Neomycin sulfate and 0.99 mg/mL NaN$_3$, pH 6.5. The concentration of TWEEN® 20® in the final ACMIA reaction mixture is approximately 0.0234%.

Preparation of Anti-tacrolimus Antibody-β-galactosidase Conjugate

Monoclonal anti-tacrolimus antibody was conjugated to β-galactosidase using a standard heterobifunctional linking agent, namely, SMCC (succinimidyl trans-4-(N-maleimidylmethyl)cyclohexane-1-carboxylate) linker according to known techniques. The antibody conjugate solution contained approximately 7.5 µg/mL anti-tacrolimus antibody-β-galactosidase conjugate 30 mg/mL protease free bovine serum albumin, 0.126 mg/mL MgCl$_2$, 0.03 mL/mL of Ethylene glycol, 35.14 mg/mL PIPES 1.5 sodium salt, 50 mg/mL NaCl and beta-gal mutein (inactivated beta-galactosidase), pH 6.5.

Magnetic Chrome Particle Preparation

The production of FK-tacrolimus chrome particles (immunoassay solid phase) proceeded by making the FK-tacrolimus-BGG (bovine gammaglobulin)-dextran conjugate, preparing a slurry with the chrome particles and then tableting the coated particles. Each FK-tacrolimus tablet contains approximately 2 mg FK-tacrolimus chrome slurry, 10.5 mg 30% bovine serum albumin (BSA), 30.4 mg trehalose dihydrate and 3.6 mg CARBOWAX® 100 µm.

Tacrolimus Assay

The principle and operation of the ACMIA assay for tacrolimus were as follows: pretreatment reagent containing one of the detergents above was added to a reaction vessel on the DIMENSION® RxL/HM instrument. Next, 20 µL of whole blood containing tacrolimus is added. The whole blood is sampled from a standard cup by first mixing the blood with the ultrasonic sample probe. The mixing of whole blood sample with the tacrolimus carbamate pretreatment solution ensured the lysis of the whole blood and the displacement of the protein bound tacrolimus molecules from their binding sites by the tacrolimus carbamate molecules. The released tacrolimus molecules therefore will be accessible to the anti-tacrolimus antibody in the reaction mixture. Anti-tacrolimus antibody-β-galactosidase conjugate (50 µL) was added next and was allowed to react with tacrolimus in the sample. The chrome particles with immobilized tacrolimus-BGG (bovine gamma globulin)-dextran were added (50 µL) and were allowed to bind the unreacted conjugate. The tacrolimus bound anti-tacrolimus antibody-β-galactosidase conjugate does not bind to the chrome but remains in the supernatant when a magnetic field was applied to the above reaction mixture to separate the solution from the chrome particles. The tacrolimus-bound conjugate was detected by transferring the supernatant from the reaction vessel to a photometric cuvette and measuring the enzymatic rate of the conjugate in the presence of chlorophenol red-β-D-galactopyranoside (CPRG). The rate was measured bichromatically at 577 and 700 nm.

Comparison of Different Pretreatment Reagents

PLURONIC® 25R2 (octylphenol ethoxylate), SDS, LDS and TRITON™ X405 (polyoxypropylene-polyoxyethylene block copolymer) were used to make separate pretreatment solutions (as discussed in detail above) for the ACMIA assay conducted on the DIMENSION® ANALYZER for measuring tacrolimus concentrations in whole blood samples containing normal and elevated cholesterol or triglyceride. Another pretreatment solution was made without the above-mentioned detergents as control for the assay ("Control"). The pretreatment solutions spiked with and without the mentioned detergents were used to prepare the reagent cartridges for the tacrolimus ACMIA assay on the DIMENSION® clinical chemistry analyzer. When the above-mentioned detergents were not used, both cholesterol and triglyceride decreased the tacrolimus recovery in the whole blood samples. In the following tables, tacrolimus recovery in ng/ml is reported. The percent cholesterol interference is reported as a negative number (since it represents a reduction in the amount of interference) and is the difference between analyte recovery with normal cholesterol and analyte recovery with high cholesterol divided by analyte recovery with normal cholesterol times 100. For example, from the Control below, the percent cholesterol interference is (10.6−3.9)÷10.6×100. The percent triglyceride interference is reported as a negative number (since it represents a reduction in the amount of interference) and is the difference between analyte recovery with normal triglyceride and analyte recovery with high triglyceride divided by analyte recovery with normal triglyceride times 100. For example, from the Control below, the percent triglyceride interference is (10.0−6.5)÷10.0×100.

Effects of SDS, LDS, PLURONIC 25R2, and TRITON 405 on Lipid Interference

| Sample/ng/mL tacrolimus measured | Control | 0.2% SDS | 0.05% LDS | 0.1% PLURONIC | 0.5% TRITON 405 |
|---|---|---|---|---|---|
| High cholesterol (400 mg/dL) | 3.9 | 10.9 | 11.9 | 10.3 | 8.9 |
| Normal cholesterol (180 mg/dL) | 10.6 | 11.9 | 12.2 | 11.1 | 11.0 |
| % Cholesterol interference | −63% | −8% | −2% | −7% | −19% |
| Elevated triglyceride (1000 mg/dL) | 6.5 | 10.9 | 11.5 | 10.5 | 9.6 |
| Normal triglyceride (200 mg/dL) | 10.0 | 11.6 | 12.2 | 10.5 | 10.8 |
| % triglyceride interference | −35% | −6% | −6% | 0% | −11% |

Effects of Other Surfactants on Lipid Interference

| Sample/ng/mL tacrolimus measured | 0.2% GAFAC | 0.1% TWEEN 20 | 0.1% ZWITTERGENT | 0.05% EP110 |
|---|---|---|---|---|
| High cholesterol (400 mg/dL) | 5.4 | 6.3 | 5.0 | 2.8 |
| Normal cholesterol (180 mg/dL) | 11.0 | 11.4 | 9.0 | 9.9 |
| % Cholesterol interference | −51% | −45% | −44% | −71% |
| Elevated triglyceride (1000 mg/dL) | 8.8 | 9.5 | 7.7 | 7.5 |
| Normal triglyceride (200 mg/dL) | 12.0 | 10.8 | 8.4 | 9.2 |
| % triglyceride interference | −27% | −12% | −8% | −18% |

When the above-mentioned detergents were formulated into the pretreatment solutions, the detergents PLURONIC® 25R2, SDS, LDS and TRITON™ X405 demonstrated sufficient mitigation of both cholesterol and triglyceride interference in accordance with embodiments of the present methods.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for enhancing the bioavailability of a hydrophobic drug in a sample suspected of containing a hydrophobic drug, the method comprising:
    (a) providing in combination in a medium:
        (i) the sample wherein the sample is from a biological fluid or a biological tissue and wherein the sample has not been treated to remove lipoproteins and
        (ii) a bioavailability agent for the hydrophobic drug, wherein the bioavailability agent comprises an ionic detergent comprising a chain of at least 10 carbon atoms or a non-ionic detergent comprising a chain of at least 15 repeating ethylene oxide units or propylene oxide units or a combination of ethylene oxide units and propylene oxide units and wherein the concentration of the bioavailability agent in the medium is sufficient to enhance the bioavailability of the hydrophobic drug by reducing interference from cholesterol and triglycerides, wherein the concentration of the bioavailability agent is about 0.0001% to about 0.5% and
    (b) incubating the medium under conditions for enhancing the bioavailability of the hydrophobic drug.

2. A method according to claim 1 for determining a hydrophobic drug in a sample suspected of containing a hydrophobic drug wherein the combination in the medium further comprises a hemolytic agent, and the method further comprises:
    (b) incubating the medium under conditions for hemolyzing cells in the sample and for enhancing the bioavailability of the hydrophobic drug,
    (c) adding to the medium reagents for determining the presence and/or amount of the hydrophobic drug in the sample wherein the reagents comprise at least one antibody for the hydrophobic drug, and
    (d) examining the medium for the presence of a complex comprising the hydrophobic drug and the antibody for the hydrophobic drug, the presence and/or amount of the complex indicating the presence and/or amount of the hydrophobic drug in the sample.

3. A method according to claim 1 wherein the hydrophobic drug is an immunosuppressant drug.

4. A method according to claim 1 wherein the bioavailability agent is a non-ionic detergent comprising a chain of at least 20 repeating ethylene oxide units or propylene oxide units or a combination of ethylene oxide units and propylene oxide units.

5. A method according to claim 4 wherein the bioavailability agent is the detergent (octylphenol ethoxylate) or (polyoxypropylene-polyoxyethylene block copolymer).

6. A method according to claim 1 wherein the bioavailability agent is an ionic detergent comprising at least 10 methylene units.

7. A method according to claim 6 wherein the bioavailability agent is sodium dodecylsulfate or lithium dodecylsulfate.

8. A method according to claim 2 wherein in step (c) an analog of the hydrophobic drug is added to the medium.

9. A method according to claim 8 wherein at least one of the antibody for the hydrophobic drug and the analog of the hydrophobic drug comprises a label.

10. A method according to claim 2 wherein in step (c) a second antibody is added to the medium wherein the second antibody binds to a complex of the hydrophobic drug and the antibody for the hydrophobic drug.

11. A method according to claim 10 wherein at least one of the antibody for the hydrophobic drug and the second antibody comprises a label.

* * * * *

UNITED STATES PATENT AND TRADEMARK OFFICE
CERTIFICATE OF CORRECTION

PATENT NO. : 7,790,401 B2
APPLICATION NO. : 11/834173
DATED : September 7, 2010
INVENTOR(S) : Wei et al.

It is certified that error appears in the above-identified patent and that said Letters Patent is hereby corrected as shown below:

In the Specifications

In column 6, line 2; change "diacylglyerol" to read --diacylglycerol--.

In column 6, line 3; change "ethanoliamin" to read --ethanolamine--.

In column 9, line 4; change "hydroxy" to read --hydroxyl--.

In column 14, line 19; change ""phthaldehyde" to read --phthalaldehyde--.

In column 22, line 12; change "florescent" to read --fluorescent--.

In column 25, line 56; change "mL/mL" to read --mg/mL--.

Signed and Sealed this
Thirtieth Day of April, 2013

Teresa Stanek Rea
*Acting Director of the United States Patent and Trademark Office*